United States Patent [19]

Bunge et al.

[11] Patent Number: 4,696,794

[45] Date of Patent: Sep. 29, 1987

[54] CL-1957D ANTIBIOTIC COMPOUND AND ITS PRODUCTION

[75] Inventors: Richard H. Bunge; James C. French; Timothy R. Hurley; Neil E. Willmer, all of Ann Arbor, Mich.

[73] Assignee: Warner-Lambert Company, Morris Plains, N.J.

[21] Appl. No.: 928,443

[22] Filed: Nov. 7, 1986

Related U.S. Application Data

[63] Continuation-in-part of Ser. No. 835,399, Mar. 3, 1986, abandoned.

[51] Int. Cl.$^4$ .......................... A61K 35/74; C12D 1/06
[52] U.S. Cl. ..................................... 424/118; 435/169
[58] Field of Search ......................... 424/118; 435/169

[56] References Cited

U.S. PATENT DOCUMENTS 4,499,075  2/1985  Lee et al. ............................. 424/118

Primary Examiner—Jerome D. Goldberg
Attorney, Agent, or Firm—Jerry F. Janssen

[57] ABSTRACT

A purified isolate of an actinomycete identified as ATCC 39366 is capable of producing the antimicrobial compound CL-1957D.

The antimicrobial compound CL-1957D is produced by cultivating isolate ATCC 39366 under aerobic conditions in a culture medium containing assimilable sources of carbon and nitrogen until a substantial quantity of the CL-1957D compound is produced, and subsequently isolating the CL-1957D compound.

The antibiotic compound CL-1957D and pharmaceutical compositions comprising this substance together with a pharmaceutically acceptable carrier is also disclosed, as are methods of treating microbial infections in mammals, employing these pharmaceutical compositions.

7 Claims, 3 Drawing Figures

CL-1957D ANTIBIOTIC COMPOUND AND ITS PRODUCTION

This application is a continuation-in-part of copending application Ser. No. 835,399 filed Mar. 3, 1986, now abandoned.

BACKGROUND OF THE INVENTION

The present invention relates to a compound demonstrating antimicrobial activity, designated CL-1957D, to pharmaceutically acceptable salts thereof, to a method of using the compounds to treat microbial infections in a mammal, and to a process for the production of said compound.

More particularly, the process of producing the CL-1957D antibiotic compound relates to an aerobic fermentation process using a purified isolate of an actinomycete, identified as isolate ATCC 39366.

SUMMARY OF THE INVENTION

Figure 1:
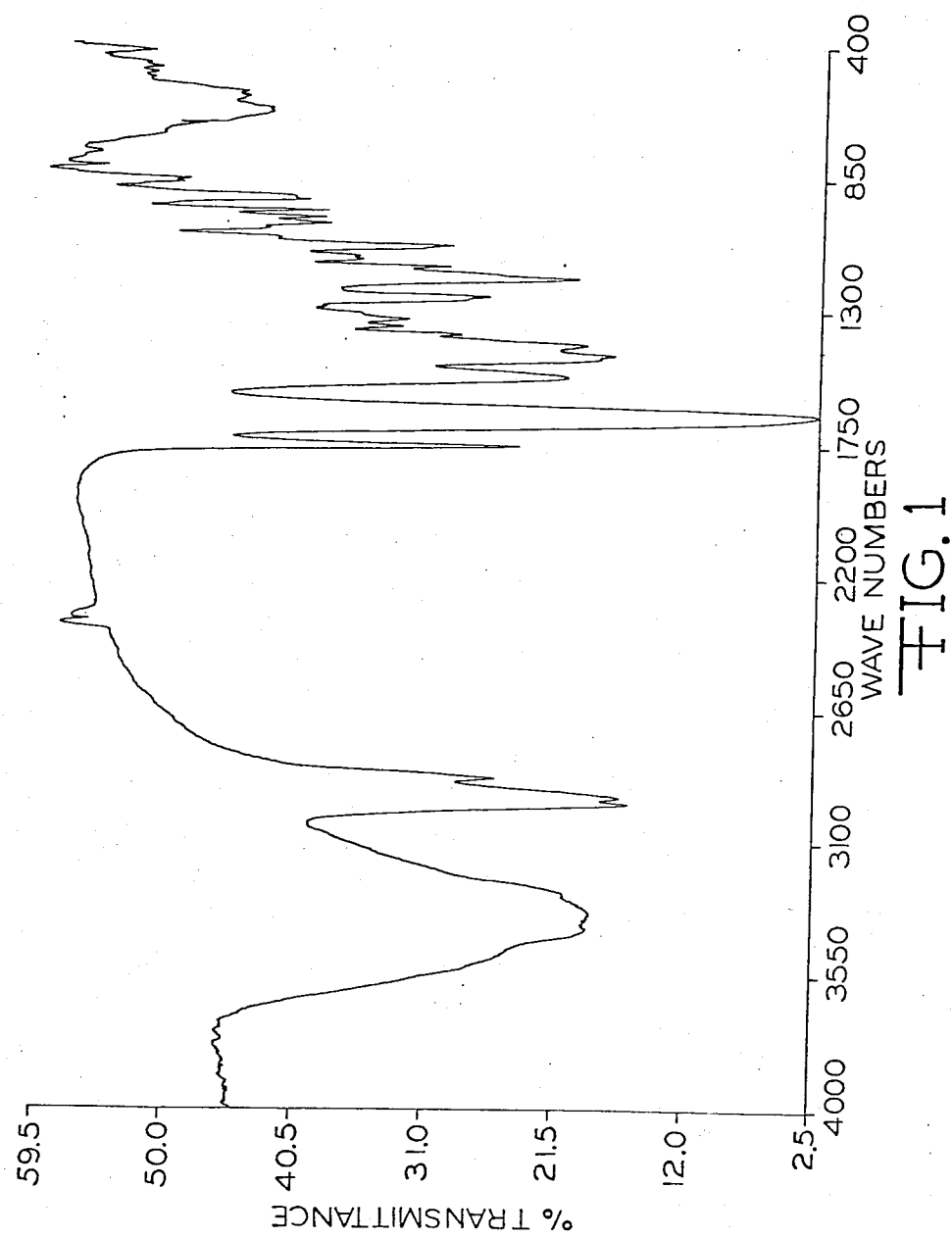
FIGS. 1, 2, and 3 are the infrared, 200 MHz proton magnetic resonance, and 75.4 MHz $^{13}$C nuclear magnetic resonance spectra, respectively, of the compound designated CL-1957D.

In accordance with one aspect of the invention, there is provided a process for producing CL-1957D by cultivating the isolate of actinomycete identified as ATCC 39366 under aerobic conditions in a medium containing assimilable sources of carbon and nitrogen until a substantial quantity of CL-1957D is produced, and subsequently isolating the CL-1957D compound.

In accordance with another aspect of the invention, there is provided the antibiotic compound CL-1957D and its pharmaceutically acceptable salts, which compounds exhibit antibiotic properties.

In another aspect of the present invention, there are provided pharmaceutical compositions useful for treating microbial infections in a mammal comprising an antimicrobially effective amount of the CL-1957D compound, or a pharmaceutically acceptable salt, together with a pharmaceutically acceptable carrier.

In a further aspect of the present invention, a method of treating microbial infections in a mammal comprises administering an antimicrobially effective amount of the compound CL-1957D or a pharmaceutically acceptable salt thereof in combination with a pharmaceutically acceptable carrier.

DETAILED DESCRIPTION

In accordance with the present invention, the CL-1957D antibiotic compound is produced by cultivating a selected isolate of actinomycete, isolate ATCC 39366, under aerobic conditions until a substantial quantity of CL-1957D is formed, and subsequently isolating the compound.

The strain of actinomycete suitable for the purpose of this invention was found in a soil sample collected in Pennsylvania, USA. This microorganism was isolated from the soil sample using a suitable agar plating medium, one containing salts such as potassium phosphate, magnesium sulfate, and ferrous sulfate, and carbon sources such as glycerol and asparagine. The strain of microorganism was plated onto the agar medium and, once plated, was incubated at a favorable temperature, particularly 45° C., to allow for the development of the soil microorganisms.

The CL-1957D producing organism that was isolated from the soil sample by the agar plating technique is an unidentified isolate of actinomycete and has been deposited with the American Type Culture Collection, Rockville, Md. 20852, where it is being maintained in their permanent culture collection as ATCC 39366. This organism, which produces CL-1957D, is also being maintained as a dormant culture in lyophile tubes, cryogenic vials, and in soil tubes in the Warner-Lambert/Parke-Davis Culture Collection, 2800 Plymouth Road, Ann Arbor, Mich. 48105, where it is designated as culture WP-2053.

Isolate ATCC 39366 was identified as a member of the Grey series of actinomycetes (cf. Table 1). The spores were produced in a spiral chain with ten or more spores in a chain. The spores were smooth and cylindrical or rectangular in shape.

TABLE 1

| Medium* | Color** |
|---|---|
| Yeast extract - malt extract agar (ISP-2) | Slate gray (aerial mycelia) Mustard gold (reverse substratal mycelium) |
| Oatmeal agar (ISP-3) | No color (aerial mycelia) Olive (reverse substratal mycelium) |
| Inorganic salts - starch agar (ISP-4) | Pewter gray (aerial mycelia) No color (reverse substratal mycelium) |
| Glycerol - asparagine | Near gray (aerial mycelia) Light wheat (reverse substratal mycelium) |

*Media compositions given in Shirling, et al., Int. J. Syst. Bacteriol., 16: 313-340 (1966).
**Color designation from Color Harmony Manual, 4th Ed., Container Corporation of America, 1958.

The cell wall of isolate ATCC 39366 contained L,L-diaminopimelic acid and glycine which are characteristic of type I cell wall. A unique feature of the organism was the presence of a major amount of arabinose which was found upon whole cell analysis.

The isolate was found to reduce nitrate, liquefy gelatin, and peptonize milk. Melanin or other soluble pigments were not formed. As shown by the data appearing in Table 2, the culture utilized ten of the sixteen carbon sources tested; it did not utilize arabinose, inulin, lactose, maltose, mannitol or sucrose.

TABLE 2

| Carbon Source | Utilization* |
|---|---|
| L-Arabinose | − |
| D-Fructose | + |
| D-Galactose | + |
| D-Glucose | + |
| Glycerol | + |
| i-Inositol | + |
| Inulin | − |
| Lactose | − |
| Maltose | − |
| D-Mannitol | − |
| D-Mannose | + |
| Raffinose | + |
| Rhamnose | + |
| Salicin | + |
| Sucrose | − |
| D-Xylose | + |
| Control (no carbon source) | − |

*"−" = No growth; "+" = Good growth.

The compound CL-1957D, which demonstrates both antibiotic and in vitro and in vivo antitumor properties, is produced by isolate ATCC 39366 during aerobic fermentation under controlled conditions. The fermentation medium consists of sources of carbon, nitrogen, minerals, and growth factors. Examples of carbon sources are glycerol and various simple sugars, such as glucose, mannose, fructose, xylose, ribose, or other carbohydrate-containing compounds such as dextrin, starch, cornmeal, and whey. The normal quantity of carbon source materials in the fermentation medium varies from about 0.1 to about 10 weight percent.

Nitrogen sources in the fermentation medium are organic, inorganic, or mixed organic-inorganic material. Examples of such materials are cottonseed meal, soybean meal, corn germ flour, corn steep liquor, distillers dried solubles, peanut meal, peptonized milk, and various ammonium salts.

The addition of minerals and growth factors are also helpful in the production of the CL-1957D compound. Examples of fermentation medium mineral additives include potassium chloride, sodium chloride, ferrous sulfate, calcium carbonate, cobalt chloride, and zinc sulfate. Sources of growth factors include various yeast and milk products.

The preferred method for producing the CL-1957D compound is by submerged culture fermentation. According to this embodiment of the invention, the fermentation ingredients are prepared in solution or suspension and the mixture subsequently sterilized by autoclaving or steam heating. The pH of the aqueous medium is adjusted to preferably between about pH 4 and about pH 8 and the mixture cooled following sterilization to a temperature between about 16° C. to about 45° C. The cooled, sterile fermentation medium is inoculated with the organism and thereafter fermentation is carried out with aeration and agitation.

In the submerged culture method, fermentation is carried out in shake-flasks or in stationary tank fermentors. In shake-flasks or in stationary tank fermentors. In shake-flasks, aeration is achieved by agitation of the flasks to bring about mixing of the medium with air. In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1957D compound is normally achieved under these conditions after a period of about two to ten days.

In an alternative embodiment, the CL-1957D compound may also be produced by solid state fermentation of the microorganism.

The following examples detailing the fermentative preparation and chemical iolation of CL-1957D are provided to enable one skilled in the art to practice the present invention and are merely illustrative thereof. They are not to be viewed as limiting the scope of the invention as defined by the appended claims.

Fermentative Production of the CL-1957D Compound

EXAMPLE 1

Stage I Seed (2-liter flask)

The contents of one lyophile tube containing the actinomycete isolate, ATCC 39366, is aseptically inoculated into one baffled 2-liter Erlenmeyer seed flask containing 600 ml of sterilized SD-14 seed medium.

The seed flask is placed on an gyrotory shaker, 130 rpm, and incubated at 24° C. After approximately 72 hours, the flask is visually inspected and checked for asepsis microscopically by wet mount and Gram stain.

TABLE 3

| Formulation of SD-14 Seed Medium | | |
|---|---|---|
| Ingredient | Amount | Supplier |
| Cerelose | 20.0 g | Corn Products |
| Torula Yeast | 2.0 g | Lake States |
| O. M. Peptone | 5.0 g | Universal Foods |
| Nutrisoy Flour | 10.0 g | Archer Daniels |
| NaCl | 1.0 g | Generic |
| CaCO$_3$ | 2.5 g | Generic |
| Deionized Water | 1000.0 ml | |

EXAMPLE 2

Stage II Seed (30-liter stirred-jar)

The contents of one Stage I seed flask is used to aspectically inoculate one stirred-jar for Stage II seed. Two stirred-jar fermentors which are 30-liter stainless steel tanks are used. Each seed stirred-jar contains 15.4 liters of SD-14 seed medium, autoclaved for 90 minutes. The seeded stirred-jars are incubated at 24° C., 300 rpm, and sparged with air at a rate of 16 liters/minute (1 volume/volume/minute). Excess foaming is monitored by a conductance probe and controlled by addition of SWS Q97 silicon antifoam (1:1 silicon oil:water) on demand. Both seed stirred-jars are sampled pre- and postinoculation and processed for pH, sedimentation (a 15 ml sample in a 15-ml conical centrifuge tube, X450G, 12 minutes), sterility (Tryptic Soy Agar plate and Nutrient Broth with pH indicator), carbohydrate (Lilly Tes-Tape glucose enzymatic test strip), and CO$_2$ (IR Detector). After approximately 48 hours, the seed stirred-jars are again sampled and processed as above. About 0.25% glucose should remain and the CO$_2$ should be in the 0.05% range.

EXAMPLE 3

Stage III Seed (757-liter fermentor)

The contents of one stirred-jar is used to aseptically inoculate one 757-liter fermentor for Stage III seed. The fermentor contains 265 liters of SD-14 seed medium, sterilized by jacket and sparger steam for 40 minutes at 121° C. The seeded fermentor is incubated at 24° C., 190 rpm, and a 7.5 cfm (0.75 volume/volume/minute) aeration rate. Excess foaming is monitored by a conductance probe and controlled by addition of SWS Q97 silicone antifoam (1:1 silicon oil:water) on demand. The seed fermentor is sampled both pre- and postinoculation as described in Example 2. After approximately 48 hours the fermentor is again sampled and processed as previously outlined. Approximately 0.25% glucose will remain and the CO$_2$ will be in the 0.06–0.07% range.

EXAMPLE 4

Production Fermentors (757-liter tanks)

Each of two stainless steel, 750-liter tanks is asceptically filled with 587 liters of PM-10A production medium which is prepared in two stages: (1) the maltose and cerelose are mixed in 55 liters of deionized water and the resulting solution is sterilized with steam for 20 minutes and (2) after cooling, this sterilized carbohydrate solution is aseptically transferred to a 757-liter tank containing the calculated volume (approximately 532 liters) of a sterilized solution of the other PM-10A ingredients. About 19 liters of the Stage II seed prepared as described in Example 3 is transferred aseptically to each of two 757-liter tanks filled with 587 liters of sterile PM-10A production medium.

The fermentation conditions are: 24° C. incubation temperature, 155 rpm impeller speed, and air sparging at a rate of 0.5-1.0 volume/volume/minute. Excess foaming is controlled (capacitance probe) by addition of SWS Q97 silicon antifoam solution (1:1 silicone oil:water) on demand. The production run time is 165 hours.

TABLE 4

| Formulation of PM-10A Production Medium | | |
|---|---|---|
| Ingredient | Amount | Supplier |
| Maltose | 15.0 g | Eastern Chemical |
| Cerelose | 10.0 g | Corn Products |
| Pharmamedia | 7.5 g | Traders Protein |
| Corn Meal | 4.0 g | Quaker Oats Co. |
| Torula Yeast | 5.0 g | Lake States |
| Deionized water adjust to pH 6.5 with NaOH | 1000.0 ml | |

EXAMPLE 5

Production Fermentor (7570-liter tank)

The production fermentor is a 7570-liter stainless steel tank charged with 4635 liters of PM-10A production medium prepared in two stages. The maltose and cerelose are mixed in 550 liters of deionized water and sterilized in situ for 20 minutes in a separate 757-liter fermentor. The remaining medium ingredients are charged into a sufficient volume of deionized water (about 3900 liters) and sterilized for 40 minutes with sparged steam at 121° C. After cooling, the presterilized carbohydrate solution is aseptically transferred to the production fermentor to provide a preinoculation volume about about 4635 liters including condensate accumulation during sterilization. The resulting medium is cooled to 24° C. and then inoculated with approximately 550 liters of the inoculation prepared in the Stage III seed fermentor from Example 3.

The fermentation conditions are: 24° C. incubation temperature, 125 rpm impeller speed, and air sparging at a rate of 0.75 volume/volume/minute. Excess foaming is controlled (capacitance probe) by addition of SWS Q97 silicone antifoam solution (1:1 silicon oil:water) on demand. The production run time is 168 hours.

Each of the production tanks is sampled pre- and postinoculation and checked for pH, sedimentation (a 15 ml sample is centrifuged in a clinical centrifuge, 450 g for 12 minutes), sterility (Tryptic Soy Agar plate, and nutrient broth with pH indicator), carbohydrate (Lilly Tes-Tape flucose enzymatic test strip), and $CO_2$ generation (IR detector).

The crude fermentation beers from two 757-liter fermentors, prepared as described in Example 4, and from one 7570-liter fermentor as described in Example 5 were harvested and the CL-1957D compound isolated as described below.

Chemical Isolation and Purification of the CL-1957D Compound

Fermentation beer (5879 liters) prepared as described in Examples 4 and 5 was adjusted to pH 3.5 with sulfuric acid and mixed for one hour with ethyl acetate (4347 liters). Celite 545 (205 kg) was added and the mixture filtered through a 79-cm plate-and-frame filter press. The filter cake was washed with ethyl acetate (491 liters) and the wash was added to the filtrate. The upper ethyl acetate layer (4082 liters) was separated and concentrated in vacuo to 54 liters. This concentrate was washed with water and then concentrated further to 15 liters. Petroleum ether (bp 30°-60° C.) (75 liters) was added and the resulting mixture was extracted with 30 liters of methanol-water (9:1) followed by a second extraction using 15 liters of methanol-water (9:1). The aqueous methanol extracts were combined (52 liters) and washed with 8 liters of petroleum ether. The remaining aqueous methanol layer was concentrated in vacuo to remove methanol. During this concentration step, dichloromethane was introduced periodically to the evaporator to afford a concentrate dissolved in 8.5 liters of dichloromethane. One fourth of this concentrate (designated Concentrate A) was diluted to 4 liters with dichloromethane and applied to a 15 cm [i.d.] × 180 cm column containing 12 kg of silicic acid-Celite 545 (1:1). After the column was washed with 67 liters of dichloromethane, the silicic acid-Celite 545 was eluted with 83 liters of dichloromethane-methanol (98:2) followed by 45 liters of dichloromethane-methanol (96:4). The former eluate was combined with the corresponding eluates obtained from the chromatography of the remaining three-quarters of Concentrate A over three separate 12 kg batches of silicic acid-Celite 545 (1:1). This combination of four eluates was concentrated in vacuo to four liters and added to the top of a 15 cm [i.d.] × 180 cm column containing 10 kg of silica gel (63-200 μm particle size, E. Merck) partially deactivated by admixture with 100 ml of water and packed in dichloromethane. After the charge was applied the column was washed with dichloromethane, and one 18-liter fraction was collected and discarded. At this point the column was developed with dichloromethane-methanol (98:2) and 13 nine-liter fractions were collected. Fractions 7-10 were pooled (36 liters) and concentrated in vacuo to a residual oil. When a solution of this product in approximately three liters of acetonitrile was allowed to stand overnight at 5° C., 184.4 g of CL-1957D precipitated as a white crystalline solid. CL-1957D can be recrystallized from actone or from aqueous ethanol with recoveries of 80% and 86%, respectively, in essentially pure form.

Figure 2:
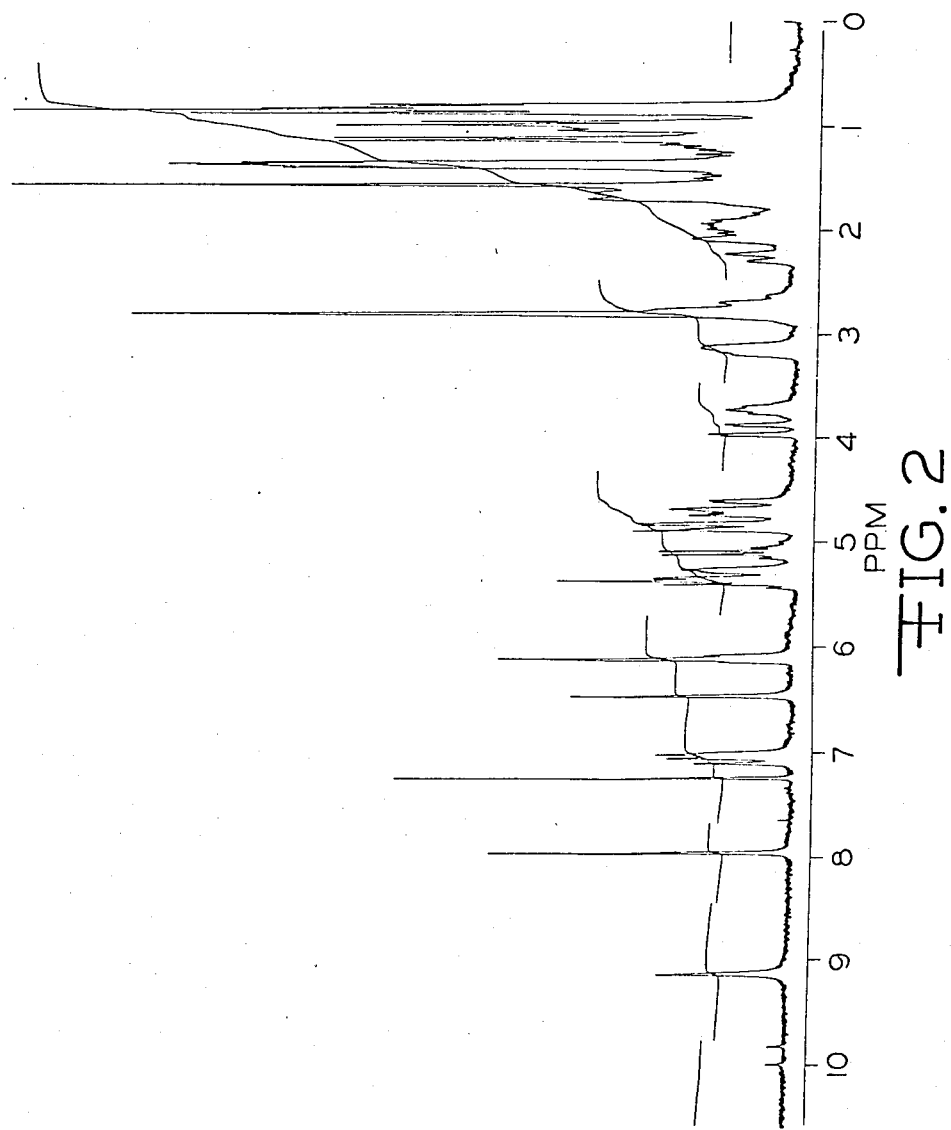
Figure 3:
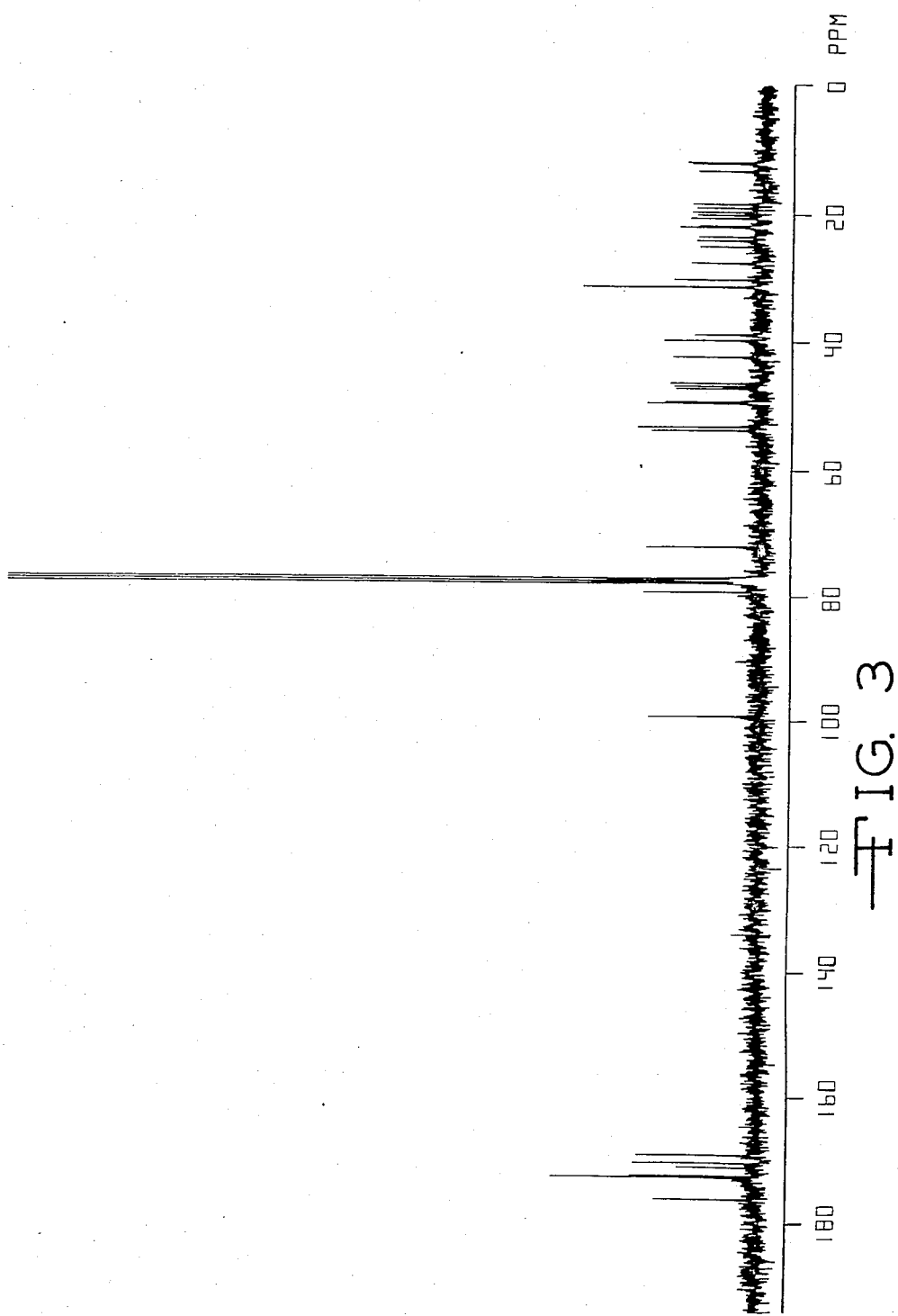

The chemical and physical properties of CL-1957D appear in Table 5 and the infrared, 200 MHz proton magnetic resonance and 70.4MHz $^{13}C$. nuclear magnetic resonance spectra of CL-1957D appear as FIGS. 1, 2, and 3, respectively.

TABLE 5

| Chemical and Physical Properties of CL-1957D | |
|---|---|
| Property | CL-1957D |
| Apparent Molecular weight (derived from FAB-mass spectroscopy) | 840 atomic mass units |
| Elemental analysis | C, 53.6%; H, 7.89%; N, 12.96%; O, 25.54% |
| Melting point | 182-184° C. |
| Optical rotation | +17.7° (1.03% in methanol) |
| Ultraviolet absorption in methanol | End absorption; no max >215 nm |
| Infrared absorption spectrum (in KBr) | Principal absorption peaks at 2972, 2954, 2877, 1754, 1643 1524, 1414, 1256, 1196, and 1803 reciprocal centimeters. |
| 200 MHz proton magnetic resonance spectrum | Principal signals at 0.78-0.87 (multiplet), 0.95-1.03 |

TABLE 5-continued

Chemical and Physical Properties of CL-1957D

| Property | CL-1957D |
|---|---|
| (deuterochloroform solution) | (multiplet), 1.20 (doublet), 1.34–1.40 (multiplet), 1.56 (singlet), 1.59–1.69 (multiplet), 1.82–2.1 (multiplet), 2.21–2.28 (multiplet), 2.67–2.79 (multiplet), 3.10–3.20 (multiplet), 3.68–3.76 (multiplet, 1 proton), 3.91 (doublet of doublets, 1 proton), 4.59–4.88 (multiplets, 4 protons), 5.04–5.15 (multi-plet, 1 proton), 5.25–5.40(multiplet), 6.07–6.15 (multiplet), 6.47 (singlet, 1 proton), 7.01–7.11 (multiplet, 2 protons), 7.96 (singlet, 1 proton), and 9.13 (singlet, 1 proton), parts per million downfield from tetramethylsilane |
| 75.4 MHz $^{13}$C nuclear magnetic resonance spectrum (deuterochloroform solution) | Principal signals at 176.03, 172.52, 172.47, 171.04, 170.28 169.17, 98.93, 78.97, 76.84, 71.75, 53.54, 52.90, 49.37, 49.04, 47.12, 46.80, 46.28, 42.13, 39.54, 38.61, 31.06, 30.97, 29.93, 27.42, 24.87, 23.89, 23.31, 21.77, 21.58, 20.38, 19.90, 19.39, 18.73, 18.18, 12.94, 11.84, and 11.64 parts per million downfield from tetramethylsilane |
| Retention time (high pressure liquid chromatography, μBondpak (TM) C-18-silica gel column, 3.9 mm i.d. × 30 cm, Waters Associates, Milford, MA, solvent: 0.05 M ammonium phosphate buffer (pH 6.5)-acetonitrile (35:65); flow rate 1.5 ml/minute | 6.1 minutes |
| $R_f$ (high performance thin-layer chromatography on silica gel 60F254, E. Merck, solvent: 90:10 chloroform-methanol-acetonitrile-28% NH$_3$ (75:9:15:1) | 0.6 |

The exact molecular structure of CL-1957D is not known but its properties assign it as a new member of the general class of antibiotics known as depsipeptides. This group of compounds consists of peptide antibiotics possessing one or more large ring lactone functionalities.

Recent example of such antibiotics are empedopeptin (reported by K. Sugawara, K. Numata, M. Konishi, and H. Kawaguchi, *Journal of Antibiotics*, Vol.37, pages 958–964, 1984) and SF-1902A (reported by S. Omoto, H. Suzuki, and S. Inouye, *Journal of Antibiotics*, Vol. 32, pages 83–86, 1979).

A review of depsipeptide antibiotics has been prepared by M. M. Shemyakin and appears in *Antimicrobial Agents and Chemotherapy*, Vol. 1965, pages 962–976 (1966).

CL-1957D can be distinguished from previously reported depsipeptides by its characteristic proton and $^{13}$C nuclear magnetic resonance spectra as well as by other properties.

Biological Activity of CL-1957D

EXAMPLE 7

The antimicrobial activity of CL-1957D was evaluated using the broth microdilution method. Serial dilutions of CL-1957D were made in Mueller-Hinton broth for bacteria and in yeast extract-peptone-dextrose broth for the Fungi. Minimal inhibitory concentrations (MICs) are listed in Table 6.

TABLE 6

| Microorganism | Culture Number | Minimal Inhibitor Concentration (MIC) of CL-1957D (μg/ml) |
|---|---|---|
| Escherichia coli | 04863 | >1000 |
| Salmonella typhimurium | TA1535 | >1000 |
| Alcaligenes viscolactis | 21698 | ≦0.46 |
| Branhamella catarrhalis | 03596 | ≦0.46 |
| Pseudomonas aeruginosa | 05111 | >1000 |
| Micrococcus luteus | 05064 | ≦0.46 |
| Staphylococcus aureus | 02482 | ≦0.46 |
| Streptococcus pyogenes | C203 | ≦0.46 |
| Streptococcus pneumoniae | SV1 | ≦0.46 |
| Streptococcus faecalis | 05045 | ≦0.46 |
| Bacillus cereus | 04810 | ≦0.46 |
| Bacillus megaterium | 066 | ≦0.46 |
| Saccharomyces cerevisiae | S288 | >1000 |
| Schizosaccharomyces pombe | M1388 | 12.3 |
| Rhodotorula aurantiaca | M1508 | >1000 |
| Torulopsis albida | M1390 | >1000 |
| Mucor parasiticus | M2652 | >1000 |
| Rhizopus japonicus | M1557 | >1000 |

EXAMPLE 8

The cytotoxicity of CL-1957D against L1210 mouse leukemia cells and against human colon adenocarcinoma (HCT8) cells was measured in vitro. The ID$_{50}$ values appear in Table 7.

TABLE 7

| Compound | L1210 Mouse Leukemia Cells | ID$_{50}$ Human Colon Adenocarcinoma Cells |
|---|---|---|
| CL-1957D | 0.0034 μg/ml | 0.0087 μg/ml |

The compound of the present invention is useful as antimicrobial agents in pharmaceutical compositions in combination with pharmaceutically acceptable carriers. These compositions may also contain other antimicrobial compounds in combination with the compound of this invention.

The compositions are made up in any pharmaceutically appropriate form for the desired route of administration. Examples of such forms include solid and liquid forms for oral administration such as tablets, capsules, powders and granules, solutions, suspensions, syrups, and elixirs, and forms suitable for parenteral administration such as sterile solutions.

For preparing pharmaceutical compositions from the compound described in this invention, inert, non-toxic, pharmaceutically acceptable carriers can be either solid or liquid. Solid form preparations include tablets, dispersable granules, capsule, cachets, and suppositories. A solid carrier can be one or more substances which may act as diluents, flavoring agents, solubilizers, lubricants, suspending agents, binders, or table disintegrating agents. Solid carriers may also be an encapsulating material.

In powders, the carrier is a finely divided solid in admixture with the finely divided active component. In tablets, the active compound is mixed with a carrier having the necessary binding properties in suitable proportions and compressed into the desired size and shape. Powders and tablets preferably contain between from 0.1 to 1.0 to about 70% of the active component, with the remainder being solid carrier.

Suitable solid carriers are magnesium stearate, magnesium carbonate, talc, sugar, lactose, pectin, dextrin, starch, gelatin, tragacanth, methylcellulose, sodium carboxymethylcellulose, low melting waxes, cocoa butter, and the like. The term "preparation" is intended to include the formulation of the active component with encapsulating material as carrier providing a capsule in which the active component (with or without other carriers) is surrounded by carrier and is thus in association with it. Similarly, cachets are also included. Tablets, powders, capsules, and cachets can be used as solid dosage forms suitable for oral administration.

For preparing suppositories, a low melting wax such as a mixture of fatty acid glycerides or cocoa butter is first melted and the active ingredient is dispersed homogeneously in the melt by stirring. The molten homogeneous mixture is then poured into molds of convenient size and shape and allowed to solidify by cooling.

Liquid form preparations include solutions, suspensions, and emulsions. Aqueous solutions for oral administration may be prepared by dissolving the active compound or one of its pharmaceutically acceptable salts in water and adding suitable colorants, flavoring agents, stabilizers, and thickening agents as desired.

Aqueous suspensions suitable form oral administration may be made by dispersing the finely divided active component in water with viscous material, i.e., a natural or synthetic gum, resin, methylcellulose, sodium carboxymethylcellulose, or other suspending agent well known in the pharmaceutical formulation art.

Also included are solid form preparations which are converted immediately prior to use for oral or parenteral adminsitration. These solid form preparations are most conveniently provided in unit dosage form and as such are used to provide a single dosage unit. Alternatively, sufficient solid may be provided such that after conversion to liquid form, multiple doses may be obtained by measuring predetermined volumes of the liquid form preparation as with a syringe, teaspoon, or other volumetric container. When multiple doses are so prepared, it is preferred that the remaining unused doses are stored at low temperature (as by refrigeration) in order to retard possible degradation of the dosage forms.

The solid form preparations intended for conversion to liquid form preparations may also contain, in addition to the active component, artificial or natural sweeteners, dispersants, stabilizers, thickening agents, solubilizing agents, and the like. The liquid employed for the preparation of liquid preparations may be water, isotonic solution, ethanol, propanol, glycerine, propylene glycol, and the like as well as mixtures thereof. Naturally, the liquid will be chosen with regard to the route of administration. For example, sterile water, sterile isotonic solution, sterile propylene glycol solutions, and the like would be employed for parenteral formulations. Preferably, the pharmaceutical composition is in unit dosage form. In such form, the preparation is dubdivided into unit doses containing appropriate quantities of the active component. The unit dosage form may be a packaged preparation, with the package containing discrete quantities of preparation, as for example in packeted tablets, capsules, or powders in vials or ampoules. The unit dosage form may also be a capsule, cachet, or tablet itself or it can be the appropriate number of any of these in packaged form.

The quantity of active compound in a unit dose of the preparation may be varied or adjusted from 0.1 to 50 mg according to the particular application in which it is used. The compositions, if desired, can also contain other compatible therapeutic agents.

In therapeutic use as an antimicrobial agent, the compound of the present invention is administered in a dosage range of from about 0.1 to 150 mg per kg of body weight per day, preferably from about 0.2 to 75 mg per kg of body weight. The dosages are varied, however, depending upon the condition and prior history of the patient and the particular condition being treated. Determination of the roper dosage for a particular situation is well within the skill of the art. Generally, treatment is initiated with smaller dosages which are less than the optimum dose of the compound, and thereafter the dose is increased by small increments until the optimum desired effect under the circumstances is achieved. For convenience, the total daily dose may be divided and administered in portions during the day if desired.

We claim:

1. An antibiotic compound designated CL-1957D or a pharmaceutically acceptable salt thereof; compound CL-1957D being characterized by:
   (a) an elemental analysis of C, 53.6%; H, 7.89%; N, 12.96%; 0, 25.54%;
   (b) a melting point of 182°–184° C.;
   (c) an optial rotation of +17.7° (1.03% in methanol);
   (d) an ultraviolet absorption spectrum that shows only end absorption in methanol;
   (e) an infrared absorption spectrum in KBr showing principal absorption peaks at 2972, 2954, 2877, 1754, 1643, 1524, 1414, 1256, 1196, and 1803 reciprocal centimeters;
   (f) a 200 MHz proton magnetic resonance spectrum in deuterochloroform solution showing principal signals at 0.78–0.87 (multiplet), 0.95–1.03 (multiplet), 1.20 (doublet), 1.34–1.40 (multiplet), 1.56 (singlet), 1.59–1.69 (multiplet), 1.82–2.1 (multiplet), 2.21–2.28 (multiplet), 2.67–2.79 (multiplet), 3.10–3.20 (multiplet), 3.68–3.76 (multiplet, 1 proton), 3.91 (doublet of doublets, 1 proton), 4.59–4.88 (multiplets, 4 protons), 5.04–5.15 (multiplet, 1 proton), 5.25–5.40 (multiplet), 6.07–6.15 (multiplet), 6.47 (singlet*, 1 proton), 7.01–7.11 multiplet, 2 protons), 7.96 (singlet*, 1 proton), and 9.13 (singlet*, 1 proton) parts per million downfield from tetramethylsilane; *exchangeable with $D_2O$;
   (g) a 75.4 $MH^{13}C$ nuclear magnetic resonance spectrum in deuterochloroform solution showing principal 176.03, 172.52, 172.47, 171.04, 170.28, 169.17, 98.93, 78.97, 76.84, 71.75, 53.54, 52.90, 49.37, 49.04, 47.12, 46.80, 46.28, 42.13, 29.54, 38.61, 31.06, 30.97, 29.93, 27.42, 24.87, 23.89, 23.31, 21.77, 21.58, 20.38, 19.90, 19.39, 18.73, 18.18, 12.94, 11.84, and 11.64 parts per million downfield from tetramethylsilane;
   (h) a retention time (high pressure liquid chromatography, µBondpak (TM) C-18-silica gel column, 3.9 mm i.d.×30 cm, Waters Associates, Milford, Ma., solvent: 0.05M ammonium phosphate buffer (pH 6.5)-acetonitrile (35:65); flow rate 1.5 ml/minute) of 6.1 minutes;
   (i) a $R_f$(high performance thin-layer chromatography on silica gel 60F254, E. Merck, solvent: chloroform-methanol-acetonitrile-28% NH$_3$ (75:9:15:1)) of 0.6.

2. A pharmaceutical composition comprising an antimicrobially effective amount of compound CL-1957D, said compound characterized as in claim 1, or a pharmaceutically acceptable salt thereof, together with a pharmaceutically acceptable carrier.

3. A pharmaceutical composition in accordance with claim 2 comprising a solution of the compound CL-1957D and absolute ethanol, said solution containing an antimicrobially effective concentration of said compound.

4. A pharmaceutical composition in accordance with claim 2 comprising a solution of the compound CL-1957D and 95% ethanol, said solution containing an antimicrobially effective concentration of said compound.

5. A pharmaceutical composition in accordance with claim 2 comprising a solution of the compound CL-1957D and propylene glycol, said solution containing an antimicrobially effective concentration of said compound.

6. A process for the production of CL-1957D as defined in claim 1 which comprises cultivating a strain of an actinomycete identified as isolate ATCC 39366, under aerobic conditions in a culture medium containing assimilable sources of carbon and nitrogen until a substantial amount of CL-1957D is produced and subsequently isolating said CL-1957D compound.

7. A method of treating microbial infections in a mammal comprising administering to said mammal in need of such treatment an antimicrobially effective amount of the compound DL-1957D as defined in Claim 1 or a pharmaceutically acceptable salt thereof in combination with a pharmaceutically acceptable carrier.

* * * * *